(12) United States Patent
Zech et al.

(10) Patent No.: US 7,186,758 B2
(45) Date of Patent: Mar. 6, 2007

(54) SILICONE-BASED DENTAL IMPRESSION COMPOUNDS

(75) Inventors: Joachim Zech, Kaufering (DE); Johann Fetz, Windach (DE); Erich Wanek, Kaufering (DE); Ingo Wagner, Worthsee (DE)

(73) Assignee: 3m ESPE AG, Seefeld (DE)

( * ) Notice: Subject to any disclaimer, the term of this patent is extended or adjusted under 35 U.S.C. 154(b) by 294 days.

(21) Appl. No.: 10/473,282

(22) PCT Filed: Mar. 28, 2002

(86) PCT No.: PCT/EP02/03527

§ 371 (c)(1), (2), (4) Date: Sep. 29, 2003

(87) PCT Pub. No.: WO02/078647

PCT Pub. Date: Oct. 10, 2002

(65) Prior Publication Data

US 2004/0110863 A1    Jun. 10, 2004

(30) Foreign Application Priority Data

Mar. 30, 2001    (DE) ................................. 101 16 223

(51) Int. Cl.
*C08K 5/01*    (2006.01)
(52) U.S. Cl. ...................... 523/109; 524/588
(58) Field of Classification Search ................ 524/588; 523/109

See application file for complete search history.

(56) References Cited

U.S. PATENT DOCUMENTS

| | | | |
|---|---|---|---|
| 3,715,334 A | 2/1973 | Karstedt | |
| 3,775,352 A | 11/1973 | Leonard, Jr. | |
| 3,814,730 A | 6/1974 | Karstedt | |
| 3,933,880 A | 1/1976 | Bergstrom et al. | |
| 4,035,453 A | 7/1977 | Hittmair et al. | |
| 4,461,854 A * | 7/1984 | Smith | 523/211 |
| 4,600,731 A | 7/1986 | Louis et al. | |
| 4,609,687 A * | 9/1986 | Schwabe et al. | 523/109 |
| 4,614,758 A | 9/1986 | Schwabe et al. | |
| 4,879,339 A | 11/1989 | Yoshino et al. | |
| 4,891,400 A | 1/1990 | Schwabe et al. | |
| 5,286,105 A | 2/1994 | Herold et al. | |
| 5,403,885 A * | 4/1995 | Voigt et al. | 524/731 |
| 5,955,513 A * | 9/1999 | Hare | 523/109 |
| 6,012,610 A | 1/2000 | Pauser et al. | |
| 6,040,354 A * | 3/2000 | Hubner et al. | 523/109 |
| 6,121,362 A | 9/2000 | Wanek et al. | |
| 6,239,244 B1 * | 5/2001 | Stepp et al. | 528/15 |
| 6,244,740 B1 | 6/2001 | Wagner et al. | |
| 6,313,190 B1 * | 11/2001 | Bublewitz et al. | 523/109 |
| 6,552,104 B1 * | 4/2003 | Hare | 523/109 |
| 6,559,199 B1 * | 5/2003 | Pusineri et al. | 523/109 |
| 2002/0147275 A1 | 10/2002 | Bublewitz et al. | |
| 2002/0156186 A1 | 10/2002 | Bublewitz et al. | |
| 2002/0197214 A1 | 12/2002 | Bublewitz et al. | |

FOREIGN PATENT DOCUMENTS

| | | |
|---|---|---|
| CA | 3406233 | 8/1985 |
| CA | 1284399 | 5/1991 |
| CA | 1285682 | 7/1991 |
| DE | 296 06 895 | 7/1997 |
| DE | 101 03 446 A1 | 8/2002 |
| DE | 101 12 9 04 A1 | 10/2002 |
| DE | 201 21 446 U1 | 11/2002 |
| DE | 101 03 446 B4 | 3/2004 |
| EP | 0 152 887 A2 | 8/1985 |
| EP | 0 158 141 A2 | 10/1985 |
| EP | 0 166 107 A2 | 1/1986 |
| EP | 0 219 660 A2 | 4/1987 |
| EP | 0 152 887 B1 | 10/1989 |
| EP | 0 158 141 B1 | 10/1989 |
| EP | 0 219 660 B1 | 11/1989 |
| EP | 0 891 763 A2 | 1/1999 |
| EP | 0 993 863 A2 | 4/2000 |
| EP | 0 891 763 B1 | 1/2003 |
| FR | 2 781 808 * | 2/2000 |
| WO | 97/40102 * | 10/1997 |

(Continued)

OTHER PUBLICATIONS

McCabe, *Applied Dental Materials*, 7th Edition, Blackwell Scientific Publications, Oxford, England, Title page, Publication page, and page 114 (1990).

(Continued)

*Primary Examiner*—Margaret G. Moore
(74) *Attorney, Agent, or Firm*—Mueting, Raasch & Gebhardt, P.A.

(57) ABSTRACT

The invention relates to a two-component addition-cured silicon impression compound, comprising the following when both components are mixed: (a) between 1 and 35 wt. % of at least one organopolysiloxane comprising at least two unsaturated groups in the molecule; (b) between 1 and 10 wt. % of at least one organohydrogenpolysiloxane comprising at least two SiH groups in the molecule; (c) between 0.00005 and 0.05 wt. % of at least one platinum catalyst, calculated as elementary platinum; (d) between 4 and 10 wt. % of at least one liquid paraffin or at least one white mineral oil, or of a mixture of at least one liquid paraffin and at least one white mineral oil; (e) between 50 and 90 wt. % of at least one filler, each respective percentage relating to the total weight of the silicon impression compound. According to the invention, one of the components before being mixed with the other component has a Brookfield viscosity ranging between 800 and 2000 Pa*s. The invention is characterized in that the silicon impression compound, when mixed, has a consistency stipulated by ISO 4823 of less then or equal to 35 mm.

15 Claims, No Drawings

FOREIGN PATENT DOCUMENTS

WO      WO 00/59453 A1      10/2000
WO      02/058641 A1      8/2002

OTHER PUBLICATIONS

International Standard, ISO 4823, "Dentistry—Elastomeric Impression Materials", Title page, Publication page, Table of Contents, Forward page and pp. 1-34 (38 pp. total) (Dec. 15, 2000).

W. Noll, *Chemistry and Technology of Silicones*, Academic Press, New York and London, Title page Publication page, Table of Contents, and Chapter 4 (pp. 124-189) (72 pages total).

W. Noll, *Chemistry and Technology of Silicones*, Academic Press, New York and London, Title page, Publication page Table of Contents, and Chapter 5 (pp. 190-245) (62 pages total).

* cited by examiner

SILICONE-BASED DENTAL IMPRESSION COMPOUNDS

The present application is a U.S. National Stage Application of PCT/EP02/03527, filed 28 Mar. 2002. The application also claims the benefit under 35 U.S.C. §119 of foreign application no. DE 101 16 223.5, filed 30 Mar. 2001.

The present invention relates to dental impression materials which are based on addition-crosslinking silicones and to a process for automatically mixing silicone-based dental impression materials. In the mixed state, these impression materials are distinguished by a putty consistency which is defined in accordance with ISO 4823 and offer a noticeably high resistance when the impression material-filled impression tray is inserted into the mouth of the patient.

In dental practice, silicone pastes are frequently used for preparing precise impressions of teeth. These silicone pastes are cold-vulcanized two-component silicone rubber systems where two pastes are blended and then crosslink after a few minutes at room temperature. Such silicone pastes can be divided into condensation-crosslinking and addition-crosslinking silicone impression materials.

When compared with condensation-crosslinking silicone impression materials, addition-crosslinking silicone impression materials exhibit substantially less contraction and therefore lead to more precise and more readily storable impressions which can be filled as frequently as desired with poured-in gypsum suspension in order to create a precise plaster model of the situation in the mouth of the patient. Addition-crosslinking silicone impression materials are therefore preferred in practice.

As a rule, such impression materials consist of two components, a basal paste, which contains silicones, filler and crosslinker, and a catalyst paste, which contains silicones, filler and catalyst. The materials are hardened after mixing has taken place in precisely defined volume ratios.

As a rule, the pastes are mixed manually or by being ejected from double-chamber cartridges, with the pastes being conveyed through a mixing tube which contains a static mixer. However, it is only possible to mix relatively small quantities of paste over a short time in this way. Since the ejection from the double-chamber cartridge is performed using a dispenser which is operated by manual force, pastes having a very high viscosity can only be mixed with very great difficulty since manual force is limited and a very high resistance to the ejection is built up as a result of the static mixer which is located in the mixing tube.

The necessity of manually mixing basal and catalyst pastes is rendered redundant by the development of automatic, motor-driven mixing and metering systems for two-component impression materials, with these systems including an automatic conveying and mixing unit, as described in U.S. Pat. No. 5,286,105. The result is a completely homogeneous product which is free of bubbles.

A two-phase molding method, in which a first impression is taken in the mouth of the patient using a firm impression material of high viscosity, is employed particularly frequently in practice. After it has hardened in the form of a crosslinked rubber, this impression is then removed from the mouth of the patient. After that, this negative form of the relevant jaw situation is subjected to further correction and definition using a readily flowing, highly precise, low-viscosity impression material and then filled by pouring in an aqueous gypsum paste which, as a plaster model in the hardened state, reproduces the jaw situation.

Addition-crosslinking silicone impression materials can be used in a number of different molding techniques and molding methods, with these materials being provided by the market and in each case having different optimal viscosities and/or consistencies and with the respective catalyst pastes having setting and working times which are adapted thereto.

ISO 4823 defines four different impression molding consistencies for this purpose, namely a readily flowing consistency (type 3), a medium-flowing consistency (type 2), a poorly flowing consistency (type 1) and a kneadable consistency (type 0).

When producing the first impression, the dentist requires a consistency which is firm and which offers a perceptible resistance when the impression tray filled with the impression material is inserted in the mouth of the patient. This resistance leads to the process of insertion being retarded, such that the dentist has to exert a certain amount of force. This thereby substantially reduces the risk of the impression tray being what is termed "pressed through". "Pressing through" is to be understood as meaning the undesirable situation in which the impression material-filled impression tray is inadvertently pushed too far in the vertical direction onto the upper jaw or the lower jaw of the patient such that the tooth surfaces come into contact with the floor of the impression tray. At these sites, the surface of the affected teeth is no longer entirely surrounded by impression material, leading to a loss of information in the negative form of the impression. Impression materials for preparing a first impression of this nature should therefore exhibit high resistance when the tray is being inserted in order to avoid this undesirable effect by means of the insertion requiring a certain degree of force such that the tray cannot be introduced too rapidly and that, during the insertion, the dentist always has control over the vertical movement in the mouth of the patient.

One possibility for preparing impression materials which exhibit resistance on introduction into the mouth consists in conferring high viscosity on the pastes. Such high viscosities are achieved, for example, in what are termed kneading materials or putty materials. These silicone impression materials are commercially available in two-component form in which metering spoons are used to remove the basal paste and the catalyst paste from correspondingly labeled containers and the lumps, which are of the same size if at all possible, are then kneaded into a homogeneous mass using the hands. In order to make these pastes kneadable, it is possible, for example, to add isoparaffin or paraffinwax or microwax and/or liquid paraffin or liquid paraffin-coated fillers to them. This prevents the pastes sticking to the fingers. Materials of this nature are described, for example, in EP-A 0 219 660, EP-A 0 166 107 A1, EP-A 0 158 141 and EP-A 0 152 887. The nonsticky consistency also results in it still being possible to shape the mixed material in the impression tray in order to be able to move a larger quantity of paste to desired sites.

In the case of these materials, it is necessary to knead the basal paste and catalyst paste manually since, because of their high viscosity, it is scarcely possible to mix them on a mixing block using a customary mixing spatula and because there is no possibility of automatic mixing and paste conveyance in a double-chamber cartridge possessing a static mixing tube.

Because the forces which arise are too high, conveying and mixing an automatic, motor-driven mixing and metering system also leads to the appliance failing. This is expressed, for example, in an unsatisfactory or inhomogeneous mixing result, a marked increase in temperature in the mixing channel, resulting in the setting reaction already starting in the mixing channel, and in the clutch of such an appliance wearing prematurely. However, it would be desirable for it also to be possible to automatically mix impression materials which had a putty-like character.

In order to achieve this, the mixing system would, for example, have to be modified appropriately, whether by increasing the conveying force or making appropriate changes to the geometry of the nozzles through which the paste to be mixed has to be pressed. The existing appliances would therefore have to be replaced with new appliances, which would have to be expensively developed from scratch, something which makes no sense economically.

One object of the present invention can therefore be seen in providing an impression material which ensures a high degree of resistance when the impression material-filled tray is being inserted into the mouth of the patient and which can be mixed homogeneously, without exhibiting the abovementioned problems, using a known, automatic, motor-driven mixing and metering system.

Another object can be seen in using impression materials having reduced viscosity, or their components, which, after mixing, exhibit a putty-like character and, after setting, exhibit a sufficiently high Shore hardness.

Accordingly, the present invention relates to a two-component addition-crosslinking silicone impression material which comprises, when the two components are in the mixed state,
(a) from 1 to 35% by weight of at least one organopolysiloxane having at least two unsaturated groups in the molecule,
(b) from 1 to 10% by weight of at least one organohydrogenpolysiloxane having at least two SiH groups in the molecule,
(c) from 0.00005 to 0.05% by weight of at least one platinum catalyst, calculated as elemental platinum,
(d) from 4 to 10% by weight of at least one liquid paraffin or at least one white mineral oil or of a mixture consisting of at least one liquid paraffin and at least one white mineral oil,
(e) from 50 to 90% by weight of at least one filler, in each case based on the total weight of the silicone impression material, with one of the components exhibiting, prior to being mixed with the other component, a Brookfield viscosity in the range from 800 to 2000 Pa*s, characterized in that, in the mixed state, the silicone impression material exhibits a consistency of less than or equal to 35 mm, as determined in accordance with ISO 4823.

The silicone impression materials according to the invention are suitable for being mechanically mixed in customary motor-driven automatic mixing appliances without the appliance itself having to be modified for this purpose, as described above. In the mixed state, the impression materials are moldable and have a nonsticky consistency.

The at least one organopolysiloxane according to (a) is more preferably present in the impression material according to the invention in a proportion in the range from 5 to 30% by weight, and particularly preferably in a range from 10 to 25% by weight.

The at least one organohydrogenpolysiloxane according to (b) is more preferably present in the impression material according to the invention in a proportion in the range from 1 to 9% by weight, and particularly preferably in a range from 1 to 8% by weight.

The at least one platinum catalyst according to (c) is more preferably present in the impression material according to the invention in a proportion in the range from 0.0001 to 0.045% by weight, and particularly preferably in a range from 0.0002 to 0.05% by weight.

The at least one liquid paraffin or at least one white mineral oil, or the mixture consisting of at least one liquid paraffin and at least one white mineral oil, according to (d) is more preferably present in the impression material according to the invention in a proportion in the range from 4.5 to 9% by weight, and particularly preferably in a range from 5 to 8% by weight.

The at least one filler according to (e) is more preferably present in the impression material according to the invention in a proportion in the range from 55 to 85% by weight, and particularly preferably in a range from 65 to 83% by weight.

Accordingly, the present invention also relates to a silicone impression material, as described above, which comprises, when the components are in the mixed state,
(a) from 10 to 25% by weight of at least one organopolysiloxane having at least two unsaturated groups in the molecule,
(b) from 1 to 8% by weight of at least one organohydrogenpolysiloxane having at least two SiH groups in the molecule,
(c) from 0.0002 to 0.04% by weight of platinum catalyst, calculated as elemental platinum,
(d) from 5 to 8% by weight of at least one liquid paraffin or at least one white mineral oil or a mixture consisting of at least one liquid paraffin and at least one white mineral oil,
(e) from 65 to 83% by weight of at least one filler, in each case based on the total weight of the silicone impression material.

In principle, the two components can be employed in any arbitrary volume ratios as long as the impression materials according to the invention are obtained. Preference is given to employing the component which exhibits a Brookfield viscosity in the range of from 800 to 2000 Pa*s in a larger proportion by volume than the other component.

Accordingly, the present invention also relates to a silicone impression material, as described above, which is characterized in that the component which, prior to mixing with the other component, exhibits a Brookfield viscosity in the range of from 800 to 2000 Pa*s is used in a larger proportion by volume than the other component.

The component which is employed in a larger proportion by volume preferably does not contain any catalyst.

In a preferred embodiment, the two components are employed in a volume ratio which is in the range from 4:1 to 6:1, more preferably in the range from 4:1 to 5:1 and particularly preferably in the range from 4.4:1 to 4.6:1.

Accordingly, the present invention also relates to a silicone impression material, as described above, which is characterized in that the two components are used in a volume ratio which is in the range from 4:1 to 6:1.

In a more preferred embodiment, the component which is employed in a higher proportion by volume has a Brookfield viscosity in the range of from 900 to 1800 Pa*s, particularly preferably in the range from 950 to 1700 and, more particularly preferred, in the range from 1000 to 1600 Pa*s.

In general, the component which is employed in a smaller proportion by volume has a Brookfield viscosity in the range of less than 1600 Pa*s, preferably in the range of from 300 to 1400 Pa*s and particularly preferably in the range from 500 to 1200 Pa*s.

Surprisingly, it has been found that it is possible to mix the two components homogeneously, in an automated manner, even when they exhibit different viscosities.

In principle, the compositions of the two components can be chosen at will as long as the impression materials according to the invention, possessing the properties according to the invention, are obtained.

In this reaction, the present invention preferably relates to a silicone impression material, as described above, which comprises, in one of the components,
(i) from 15 to 20% by weight of at least one organopolysiloxane having at least two unsaturated groups in the molecule,
(ii) from 1 to 10% by weight of at least one organohydrogenpolysiloxane having at least two SiH groups in the molecule,
(iii) from 5 to 8% by weight of at least one liquid paraffin or at least one white mineral oil, or of a mixture consisting of at least one liquid paraffin and at least one white mineral oil,
(iv) from 60 to 80% by weight of at least one filler, in each case based on the total weight of this component, with this component exhibiting a Brookfield viscosity in the range of from 800 to 2000 Pa*s, and, in the other component,
(i') from 5 to 20% by weight of at least one organopolysiloxane having at least two unsaturated groups in the molecule,
(ii') from 0.00005 to 0.05% by weight of at least one platinum catalyst, calculated as elemental platinum,
(iii') from 0.5 to 6% by weight of at least one liquid paraffin or at least one white mineral oil, or a mixture consisting of at least one liquid paraffin and at least one white mineral oil,
(iv') from 60 to 80% by weight of at least one filler, in each case based on the total weight of this component.

As far as the constituent according to (a) or (i) or (i') is concerned, it can consist either of one organopolysiloxane or of several organopolysiloxanes which differ from each other. Thus, for example, the constituent according to (i) can contain one organopolysiloxane and the constituent according to (i') can contain the same organopolysiloxane or an organopolysiloxane which differs from it. It is likewise possible, for example, for the constituent according to (i) or (i') to contain one organopolysiloxane and the constituent according to (i') or (i) to contain two or more organopolysiloxanes of which, for example, one can be the same as that of the constituent (i) or (i'). It is likewise possible for the constituent according to (i) to contain two or more organopolysiloxanes and the constituent according to (i') to contain two or more polysiloxanes, with it being possible for all the organopolysiloxanes to differ from each other.

Particular preference is furthermore given to using a combination of at least two linear dimethylvinylsiloxy-terminated polydimethylsiloxanes which are of differing viscosity and whose structure is described below.

The combination preferably comprises one representative of high viscosity, preferably in the range of from 60,000 mPa*s to 500,000 mPa*s, particularly preferably in the range of from 70,000 to 200,000 mPa*s, and more particularly preferably in the range from 80,000 to 150,000 mPa*s, and one representative of low viscosity, preferably in the range of from 25 to 1000 mPa*s, particular preferably in the range of from 50 to 500 mPa*s and more particularly preferably in the range of from 100 to 300 mPa*s.

Accordingly, the present invention also relates to a silicone impression material, as described above, which is characterized in that the constituent (a) or the constituent (i) or the constituent (i'), or both the constituent (i) and the constituent (i') comprise(s) at least two organopolysiloxanes which differ from each other and which have at least two unsaturated groups in the molecule, where
at least one organopolysiloxane has a viscosity in the range of from 25 to 1000 mPa*s, and
at least one organopolysiloxane has a viscosity in the range of from 60,000 to 500,000 mPa*s.

In a more preferred embodiment, the present invention relates to a silicone impression material, as described above, which is characterized in that constituent (a) contains the at least one organopolysiloxane, having a viscosity in the range of from 25 to 1000 mPa*s, in a proportion in the range of from 1 to 5% by weight and the at least one organopolysiloxane, having a viscosity in the range of from 60,000 to 500,000 mPa*s, in a proportion in the range of from 10 to 20% by weight.

In an embodiment which is likewise preferred, the constituent according to (a) also contains at least one organopolysiloxane having an average viscosity in the range of from 2000 to 50,000 mPa*s, preferably in the range of from 5000 to 20,000 mPa*s, and particularly preferably in the region of about 10,000 mPa*s. In this connection, it is possible, inter alia, for this at least one organopolysiloxane to be present either in the constituent according to (i) or in the constituent according to (i') or in these two constituents, with it also being possible to employ two or more of these organopolysiloxanes which differ from each other.

In general, the parts by weight ratios of the low-viscosity representative according to constituent (a) to the high-viscosity representative according to constituent (a) are in the range of from 1:2 to 1:20, preferably in the range of from 1:2.5 to 1:10, particularly preferably in the range of from 1:3 to 1:8 and very particularly preferably in the range of from 1:3 to 1:5. If a medium-viscosity representative according to (a) is additionally employed, the ratios by weight for this representative as compared with the high-viscosity representative are preferably in the range of from 1:2.5 to 1:10, particularly preferably in the range of from 1:3 to 1:8 and very particularly preferably in the range of from 1:5 to 1:8.

The constituent according to (a) and, respectively, (i) and (i') is preferably at least one diorganopolysiloxane having terminal triorganosiloxy groups, of which at least one is a vinyl group.

Preferred diorganopolysiloxanes of this structure are depicted by the following formula

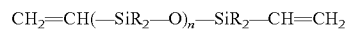

in which R represents an unsubstituted or substituted monovalent hydrocarbon group which is preferably free from aliphatic multiple bonds, and n represents an integer. Preference is given to at least 50% of the radicals R being methyl groups. Examples of other R groups are ethyl, vinyl and 3,3,3-trifluoropropyl groups. The value of n is preferably selected such that the polymer has a viscosity at 25° C. which is in the range of from 25 to 500,000 mPa*s. Molecules of this nature are described in U.S. Pat. No. 4,035,453, whose entire disclosure in this regard is hereby incorporated by reference into the present application.

The constituents according to (a) or (i) or (i') are prepared using customary methods which are described, for example, in W. Noll, "Chemie und Technologie der Silikone" [Chemistry and Technology of the Silicones]", Verlag Chemie Weinheim, 2nd Edition 1964, pages 162–206.

Particular preference is given to linear polydimethylsiloxanes which are of the above structure, which are in the abovementioned viscosity ranges and in which the end groups consist of dimethylvinylsiloxy units and the other R substituents in the chain consist of methyl groups.

The representative having a low viscosity is preferably present in a proportion which is in the range from 1 to 5% by weight, based on the total weight of the mixed silicone impression material.

The fillers (e) which can be used are preferably nonreinforcing fillers having a BET surface of up to 50 m$^2$/g, such as quartz, cristobalite, calcium silicate, zirconium silicate, montmorillonites, bentonites, zeolites, including the molecular sieves, such as sodium aluminum silicate, metal oxide powders, such as aluminum or zinc oxides or their mixed oxides, barium sulfate, calcium carbonate, gypsum and glass and plastic powders. Particular preference is given to quartz, cristobalite and sodium aluminum silicates which can be surface-treated.

Accordingly, the present invention also relates to a silicone impression material, such as described above, which is characterized in that the at least one filler according to (e) exhibits a BET surface area of up to 50 m$^2$/g.

In a particularly preferred embodiment, the fillers according to (e) exhibit a BET surface area of up to 10 m$^2$/g.

All the BET surface areas which are specified in this application refer to measurements which were carried out in accordance with DIN 66132.

Possible fillers also include reinforcing fillers having a BET surface area of greater than 50 m$^2$/g, such as pyrogenic or precipitated salicic acid, such as Aerosil and silicon aluminum mixed oxides.

Within the context of the present invention, it is possible, for example, to use both reinforcing and nonreinforcing fillers, with, for example, at least one reinforcing filler being present in one of the components and at least one nonreinforcing filler being present in the other component. It is likewise also possible for reinforcing and nonreinforcing filler to be present together in one single component or to be present in both components, with it being possible for reinforcing fillers which are different from each other, or different nonreinforcing fillers, to be present in the different components.

In a preferred embodiment of the impression materials according to the invention, the fillers are selected such that the at least one reinforcing filler is present in a proportion which is in the range of from 0.00001 to 5%, based on the total filler content of the impression material. More preferably, this proportion is in a range of from 0.1 to 4% and particularly preferably in a range of from 0.3 to 3%.

Said fillers can be surface-treated and, in this connection, preferably hydrophobized, for example by being treated with organosilanes or organosiloxanes or by hydroxyl groups being etherified to give alkoxy groups.

In principle, the quantities of filler are to be selected such that the hardened silicone impression materials achieve a Shore hardness A which is in the range of from 40 to 80, preferably in the range of from 60 to 75.

All the Shore hardness A values which are mentioned in this application are values which are determined in accordance with DIN 53505.

The abovementioned fillers can also be used for adjusting the rheological properties of the silicone impression materials. It is furthermore also possible to regulate the respective Theological properties of the individual components, i.e. the basal component and the catalyst component.

An advantage of using at least two different viscose constituents according to (a) and, respectively, (i) and (i'), as described above, is to be seen, inter alia, in the fact that this makes it possible to adjust the rheological properties of the silicone impression materials. It is furthermore also possible to regulate the respective rheological properties of the individual components, i.e. the basal component and the catalyst component.

Accordingly, the present invention also relates to the use
of a mixture of at least two organopolysiloxanes having at least two unsaturated groups in the molecule, where
at least one organopolysiloxane has a viscosity in the range of from 25 to 1000 mPa*s, and
at least one organopolysiloxane has a viscosity in the range of from 60,000 to 500,000 mPa*s, or
of at least one filler having a BET surface area of up to 50 m$^2$/g, or
of both these at least two organopolysiloxanes and this at least one filler as constituents of a silicone impression material or of at least one of the two components, as described above, for adjusting the Theological properties of the silicone impression material or components.

In particular, the present invention describes the use of these organopolysiloxanes for adjusting the Theological properties of two-component, addition-crosslinking silicone impression materials of the type in accordance with ISO 4823, thereby making it possible for these impression materials to be discharged using motor-driven mixing systems, something which is in particular the case at prevailing ejection forces of up to 4000 N. It has been found that, in order to achieve a serviceable mixing result without mechanically impairing the mixing appliance, the cartridges, the tubular bags or the mixer, the conveying force, which is transmitted, by way of the pistons, to the pastes to be mixed, should advantageously not significantly exceed the magnitude of about 4000 N.

The magnitude of the ejection force is determined in a ZWICK universal testing apparatus. Tubular bags filled with basal paste and catalyst paste are inserted into the corresponding cartridges. The filled cartridge is inserted into a testing device which essentially consists of an electrically driven discharging unit, which is mounted on a (Zwick) universal testing apparatus.

The measurement is carried out as follows: the force for conveying the paste, which force acts on the piston plates of the discharging unit, is not exerted by way of the motor of the original discharging unit but, instead, by way of the feeding unit of the universal testing apparatus. This makes it possible to measure the total force which is exerted (pressure sensor, 10 KN load cell, feeding rate 23 mm/min). A mixer as described in German patent application DE-A 101 12 904.1 is used in the measurement. This mixer is driven by way of the mixer shaft of the discharging unit. The value which is obtained after a feeding distance of 30–50 mm is that which is relevant for determining the ejection force.

The present invention therefore also relates to the above-described use, which is characterized in that the rheological properties lead to ejection forces of at most 4000 N in an automatic mixing unit which is used for discharging the components and the silicone impression material.

Surprisingly, it has been found that, by adding, as constituent, a mixture of organopolysiloxanes, which possess at least one reactive vinyl group and particular viscosity values, to a two-component addition-crosslinking silicone impression material, the overall viscosity of the mixed paste can be regulated and, in particular, lowered such that the components or materials can be automatically mixed in, and discharged from, an electrically driven mixing unit without loosing their putty character (moldability, nonstickiness and resistance on introduction into the mouth).

As an approximation, the resistance on inserting the impression tray filled with mixed impression material can be described by the resistance which is exerted solely by the paste which is present in higher volume. This view offers the advantage that the contributions of the paste present at lower volume, which paste only has a relatively small share in terms of volume in the mixed paste in a 4.5:1 system, are eliminated.

The resistance of the higher-volume paste on inserting the tray can be described, by way of example, by the Brookfield viscosity measurement, in which the resistance of the paste is measured against the rotatory motion of an inserted metal cross having defined vein lengths. The viscosity can, for example, be determined using a Brookfield DV III rheometer (HB 5 spindle, vein width 15.5 mm, speed 5 rpm, readout 20 sec after starting).

Specifically, the viscosity is determined at 23° C. in the following manner: after having been switched on and adjusted, the rheometer is fitted with the HB 5 measuring spindle (vein width=15.5 mm). After that, the paste which is to be measured, and which has the larger share of the volume, is first of all kneaded with the hands for 40 sec and then aliquoted into a measuring beaker such that it is free of bubbles; material which is packed in tubular bags is aliquoted directly from a commercially available mixing unit (Pentamix® 2, from ESPE) into a measuring beaker whose diameter is at least 20 mm in order to avoid effects which may stem from the beaker wall. The filling height should be at least 30 mm. After that, and without any time delay, the filled measuring beaker is placed in the beaker clamping stand and the measuring spindle is lowered centrally into the paste to a depth of 25 mm. The test-is now started. The measured value, which is shown in the display as centipoise (corresponds to mPa*s), is readout 20 sec after starting the measurement. Care must be taken to ensure that the measuring beaker is at no time during the measurement entrained by the rotation of the spindle. This provides a viscosity value in Pa*s, which is a direct measurement of the resistance which the paste offers to movement against a foreign body. A mean value obtained from at least 5 measurements is used. This value correlates with the resistance to insertion of the impression tray, where the teeth of the patient constitute the solid bodies. However, the value also provides a correlation with the resistance which the paste offers to conveyance and mixing in automatic, motor-driven mixing units since, in this case, too, the flow channels and the mixing blades within the mixing unit move the paste and deflect its direction of flow several times.

Within the context of the present application, the term "Brookfield viscosity" is understood as being a viscosity which has been measured as described above.

The viscosity data for constituents (a), (b) and (d) are dynamic viscosities which are measured at 20° C. in accordance with DIN 53018 or 51562, with the viscosities of the constituents according to (a) and (b) being determined in accordance with DIN 53018 and the constituents according to (d) being determined in accordance with DIN 51562.

The constituent according to (b) is preferably at least one organopolysiloxane having at least 3 Si-bonded hydrogen atoms per molecule. This organopolysiloxane preferably contains from 0.01 to 2% by weight of silicon-bonded hydrogen. The silicone valences which are not saturated with hydrogen or oxygen atoms are saturated with monovalent hydrocarbon radicals which are free from aliphatic multiple bonds. The hydrocarbon radicals can be substituted or unsubstituted. At least 50%, preferably 100%, of the hydrocarbon radicals which are bonded to silicon atoms consist of methyl radicals. The structure and preparation of such components are also described in the abovementioned literature references.

The quantitative proportions of constituents (a) and (b) are preferably selected such that from 0.75 to 5 mol of SiH units in accordance with (b) is/are present per mol of unsaturated double bond in accordance with (a). The sum of the constituents (a) and (b) is in a range of from 10 to 40% by weight, preferably from 15 to 25% by weight, based on the total weight of all the constituents in the silicone impression material.

The constituent according to (c) is preferably a platinum complex which, once again preferably, can be prepared from hexachloroplatinic acid by reduction with tetramethyldivinylsiloxane. Other platinum compounds which accelerate the addition crosslinking are also suitable. Platinum-siloxane complexes, as described in U.S. Pat. Nos. 3,715,334, 3,775,352 and 3,814,730 are, for example, well suited for this purpose. The platinum catalyst is preferably employed in quantities in the range of from 0.00005 to 0.05% by weight, in particular in the range of from 0.0002 to 0.04% by weight, particularly preferably in the range of from 20 to 100 ppm by weight, and more particularly preferably in the range of from 25 to 60 ppm by weight, in each case calculated as elemental platinum and based on the total weight of all the constituents in the silicone impression material. It is possible to use two or more platinum catalysts if this would be expedient.

In order to control reactivity, it is possible to add an inhibitor which impedes premature crosslinking to form the elastomer. Inhibitors of this nature are described, for example, in U.S. Pat. No. 3,933,880. Examples of these inhibitors are, inter alia, acetylenically unsaturated alcohols, such as 3-methyl-1-butyn-3-ol, 1-ethylvinylcyclohexan-1-ol and 3-methyl-1-pentyn-3-ol. Examples of vinylsiloxane-based inhibitors are, inter alia, 1,1,3,3-tetramethyl-1,3-divinyldisiloxane and vinyl group-containing oligosiloxanes and disiloxanes, which are preferably added in quantities in the range of from 0.00001 to 0.2% by weight, based on the total weight of all the constituents in the silicone impression material.

In addition, the impression materials according to the invention can, where appropriate, contain at least one customary additive. Examples of such customary additives are plasticizers, silicone oils, pigments, antioxidants and mold release agents. It is likewise also possible for finely divided palladium or platinum to be present as a hydrogen absorber. In this connection, the metals can, if necessary, also be applied to suitable support materials. These customary additives are preferably present in the impression material according to the invention in a proportion which is in the range of from 0.0001 to 2% by weight.

Accordingly, the present invention also relates to a silicone impression material, as described above, which is characterized in that it additionally comprises inhibitor, in a proportion in the range of from 0.00001 to 0.2% by weight, or at least one customary additive, in a proportion in the range of from 0.00001 to 2% by weight, or a mixture of inhibitor and at least one customary additive, in a proportion of from 0.00002 to 2.2% by weight, in each case based on the total weight of the silicone impression material.

The constituent according to (d) is at least one liquid paraffin or white mineral oil or a mixture thereof which, at room temperature, constitutes a liquid mixture of alkanes having a viscosity of preferably from 100 to 400 mPa*s at 20° C., particularly preferably from 110 to 300 mPa*s and more particularly preferably between 120 to 250 mPa*s. Preference is given, in this connection, to using grades which are, for example, to a large extent freed, by hydrogenation, from aromatic polycyclic hydrocarbons and which mainly have a carbon chain distribution of between approx. 15 and 50 carbon atoms.

Accordingly, the present invention also relates to a silicone impression material, as described above, which is characterized in that the at least one liquid paraffin or the at least one white mineral oil, or the mixture composed of at least one liquid paraffin and at least one white mineral oil, according to (d) has a viscosity at 20° C. which is in the range of from 100 to 400 mPa*s.

It is surprisingly possible for the mixed paste not to be sticky even though, for example, the low-volume paste can on its own stick to the hands.

A method for using automatic, motor-driven mixing units to mix impression materials which are kneadable in accordance with ISO 4823 is likewise in accordance with the invention.

The present invention therefore also relates to a method for mixing a silicone impression material which is characterized in that the two components are mixed using an automatic, motor-driven mixing unit.

In particular, the present invention relates, in this connection, to a method, as described above, which is characterized in that it comprises the following steps:

(A) introducing the components which are contained in primary packs into secondary packs which are compatible with the dimensions of the automatic mixing unit, or
introducing the components which are contained in primary packs directly into the automatic mixing unit, or
introducing one of the components which is contained in a primary pack into a secondary pack which is compatible with the corresponding dimensions of the automatic mixing unit and directly introducing the component contained in a primary pack into the automatic mixing unit;
(B) discharging the components from the automatic mixing unit by way of a dynamic small mixing tube, while mixing the components, at ejection forces of at most 4000 N.

PREPARATION EXAMPLE

A basal paste was prepared in a customary laboratory kneading machine by combining, to homogeneity, 17.1 parts by weight of a vinyl-terminated polydimethylsiloxane having a viscosity of 1000 mPa*s, 1.8 parts of a vinyl-terminated polydimethylsiloxane having a viscosity of 200 mPa*s, 3.6 parts of a polymethylhydrogensiloxane having a viscosity of 50 mPa*s and 6.6 parts of a liquid paraffin having a viscosity of 130 mPa*s with 70.7 parts by weight of a hydrophobized quartz powder having an average particle size of 4 μm and 0.2 parts of the coloring paste FL Dunkelblau [FL dark blue] (Wacker Chemie).

A catalyst paste was produced by mixing 13.3 parts of a vinyl-terminated polydimethylsiloxane having a viscosity of 10,000 mPa*s, 5.6 parts of a vinyl-terminated polydimethylsiloxane having a viscosity of 200 mPa*s, 4 parts of a liquid paraffin having a viscosity of 130 mPa*s, 2.2 parts of a solution of a platinum complex mixture in silicone oil having a content of platinum by weight of about 1%, and 0.9 parts of an inorganic coloring pigment (Sicomet Grün [Sicomet green], BASF) with 74 parts of a sodium silicate filler having an average particle size of 2 μm.

Application Example

Tubular bags were filled with 300 ml of basal paste and 66 ml of catalyst paste in accordance with the preparation example. These tubular bags were then introduced into an ESPE, Seefeld, Pentamix® 2 mixing unit. When a mixer in accordance with patent application DE-A 101 12 904.1 was used, it was possible to convey both pastes, in a homogeneous mixture, from the unit without the unit clutch slipping. The Brookfield viscosity of the basal paste was 1500 Pa*s. Prior to the mixing, the basal paste did not stick to the fingers while the catalyst paste, by contrast, did adhere to the fingers. The mixed paste was not sticky and could be molded with the fingers in the impression tray even though the catalyst paste on its own adhered to the fingers. In the mixed state, it was possible to observe a perceptible increase in viscosity after about 2 min. After about 6 min, the mixture was present as a hardened rubber. The Shore hardness A of the rubber (measured in accordance with DIN 53 505) was 70, when measured 30 min after mixing. The consistency as determined in accordance with ISO 4823 was 28 mm.

Comparison Experiments

Comparison experiments using commercially available modeling materials showed (table 1) that their higher-volume pastes have Brookfield viscosities of at least 2000 Pa*s. The previously described experiment for discharging the pastes from an automatic mixing unit led to failure of the unit.

TABLE 1

| Product (Manufacturer) | Brookfield viscosity Basal paste | Catalyst paste | Consistency in accordance with ISO 4823 [mm] | Batch No. |
|---|---|---|---|---|
| Dimension ® Penta H Quick (3M ESPE AG) *# | 744 | 600 | 29 | 254/2002.01 |
| Silagum ® Putty Soft (DMG) *# | 770 | | 31 | 90023/2002.03 |
| Preparation example # | 1480 | 640 | 28 | 002 |
| Blend-A-Gum ® Body (Densply) | 2160 | 3624 | 25 | 6000177/2001.10 |
| Reprosil ® Easy Mix Putty (Dentsply) | 2370 | 3000 | 27 | 3001948/2002.09 |
| Permagum ® (3M ESPE AG) | 2640 | | 26 | 081/2002.12 |
| Flexitime ® Easy Putty (Heraeus Kulzer) | 3008 | 2770 | 29 | 130342/2002.04 |
| Exaflex ® Putty (GC) | 3320 | 2680 | 26 | 121198A |
| Panasil Putty (Kettenbach) | 3790 | 2632 | 25 | 6898 |

All Brookfield viscosity values in Pa*s.
The comparison products labeled * are commercially available silicone impression materials which were conveyed out of the Pentamix ® 2 mixing unit but which do not exhibit any high resistance on being introduced into the mouth and stick to the fingers in the mixed state and were consequently not moldable using the fingers.
The products marked # are products which were mixed in the Pentamix ® mixing unit in the volume ratio of 4.5:1.
The products which are not marked with # are commercially available putty modeling materials in a volume ratio of 1:1.

An ejection experiment using the product Blend-A-Gum (batch # 0006000177) is described by way of example.

Tubular bags which are compatible with the ESPE Pentamix® system were filled with basal paste and catalyst paste, with the base to catalyst volume ratio being 4.5:1. The tubular bags were sealed and inserted into commercially available Pentamix® cartridges after they had been provided with standardized outlet caps, as described in DE-A 296 06 895, which are self-opening in the Pentamix® appliance (opening diameters, inlet for basal paste 8.6 mm, inlet for catalyst paste 2.3 mm). The pastes were ejected using a Pentamix® 2 unit and employing a mixer as described in DE-A 101 12 904.1. The mixer corresponds to the mixer which is described in EP-A 0 993 863.

For comparison, the paste according to the invention, as described in the above preparation example, was ejected using the same system.

After 20 g of the comparison material had been discharged from the mixing unit, it was already possible to note a marked increase of temperature in the unit to approx. 40° C. It was not possible to completely fill a maxillary impression tray (quantity of material required, approx. 40 g) since the material to be mixed already began to set in the small mixing tube and the conveyance of the paste through the mixing machine no longer functioned due to the forces being too high. After a quantity of 20 g had been conveyed, the ejection forces were greater than 4900 N.

By contrast, it was possible to eject and mix the material according to the invention, as described in the application example, without any difficulty, with a temperature peak of 35° being observed and a conveying rate of 130 g/min being achieved. The mixture was of homogeneous and bubble-free quality. When using the abovementioned mixer, the ejection forces which had to be applied amounted to 3500 N.

The invention claimed is:

1. A two-component addition-crosslinking silicone impression material comprising a first component and a second component, wherein the material, when the two components are in the mixed state, comprises:
    (a) from 1 to 35% by weight of a mixture of at least one organopolysioxane having at least two unsaturated groups in the molecule and having a viscosity in the range of from 25 to 500 mPa*s at 25° C., and at least one organopolysiloxane having at least two unsaturated groups in the molecule and having a viscosity in the range of from 60,000 to 500,000 mPa*s at 25° C.,
    (b) from 1 to 10% by weight of at least one organohydrogenpolysiloxane having at least two SiH groups in the molecule,
    (c) from 0.00005 to 0.05% by weight of at least one platinum catalyst, calculated as elemental platinum,
    (d) from 4 to 10% by weight of at least one liquid paraffin or at least one white mineral oil or of a mixture consisting of at least one liquid paraffin and at least one white mineral oil,
    (e) from 50 to 90% by weight of at least one filler, in each case based on the total weight of the silicone impression material, with one of the components exhibiting, prior to being mixed with the other component, a Brookfield viscosity in the range from 800 to 2000 Pa*s at 23° C., characterized in that, in the mixed state, the silicone impression material exhibits a consistency of less than or equal to 35 mm, as determined in accordance with ISO 4823.

2. A silicone impression material as claimed in claim 1 which comprises, when the components are in the mixed state,
    (a) from 10 to 25% by weight of a mixture of at least two organopolysiloxanes having at least two unsaturated groups in the molecule, where at least one organopolysiloxane has a viscosity in the range of from 25 to 500 mPa*s at 25° C., and at least one organopolysioxane has a viscosity in the range of from 60,000 to 500,000 mPa*s at 25° C.,
    (b) from 1 to 8% by weight of at least one organohydrogeupolysiloxane having at least two SiH groups in the molecule,
    (c) from 0.0002 to 0.04% by weight of platinum catalyst, calculated as elemental platinum,
    (d) from 5 to 8% by weight of at least one liquid paraffin or at least one white mineral oil or a mixture consisting of at least one liquid paraffin and at least one white mineral oil,
    (e) from 65 to 83% by weight of at least one filler, in each case based on the total weight of the silicone impression material.

3. A silicone impression material as claimed in claim 1, wherein the component which, prior to mixing with the other component, exhibits a Brookfield viscosity in the range of from 800 to 2000 Pa*s at 23° C. is used in a larger proportion by volume than the other component.

4. A silicone impression material as claimed in claim 1, wherein the volume ratio of the first component to the second component is in the range of from 4:1 to 6:1.

5. A silicone impression material as claimed in claim 1, which additionally comprises at least one inhibitor, with a proportion in the range of from 0.00001 to 0.2% by weight, or at least one additive, with a proportion in the range of from 0.00001 to 2% by weight, or a mixture composed of at least one inhibitor and at least one additive, with a proportion of from 0.00002 to 2.2% by weight, in each case based on the total weight of the silicone impression material.

6. A silicone impression material as claimed in claim 1, wherein the at least one liquid paraffin or the at least one white mineral oil or the mixture composed of at least one liquid paraffin and at least one white mineral oil in accordance with (d) has a viscosity at 20° C. which is in the range of from 100 to 400 mPa*s.

7. A silicone impression material as claimed in claim 1, wherein the at least one filler according to (c) has a BET surface area of up to 50 m$^2$/g.

8. A silicone impression material as claimed in claim 1 which comprises at least 2 fillers according to (e) which differ from each other, wherein at least one filler has a BET surface area of up to 50 m$^2$/g and at least one filler has a BET surface area of more than 50 m$^2$/g.

9. A silicone impression material as claimed in claim 1, which comprises, in one of the components,
    (i) from 15 to 20% by weight of at least one organopolysiloxane having at least two unsaturated groups in the molecule,
    (ii) from 1 to 10% by weight of at least one organohydrogenpolysioxane having at least two SiH groups in the molecule,
    (iii) from 5 to 8% by weight of at least one liquid paraffin or at least one white mineral oil, or of a mixture consisting of at least one liquid paraffin and at least one white mineral oil,
    (iv) from 60 to 80% by weight of at least one filler, in each ease based on the total weight of this component, with this component exhibiting a Brookfield viscosity in the range of from 800 to 2000 Pa*s at 23° C., and, in the other component, (i') from 5 to 20% by weight of at least one organopolysioxane having at least two unsaturated groups in the molecule, (ii') from 0.00005 to 0.05% by weight of at least one platinum catalyst, calculated as elemental platinum, (iii') from 0.5 to 6% by weight of at least one liquid paraffin or at least one white mineral oil, or a mixture consisting of at least one liquid paraffin and at least one white mineral oil, (iv') from 60 to 80% by weight of at least one filler, in eaeh case based on the total weight of this component, where either the constituent (a) or the constituent (i) or the constituent i', or both the constituent (i) and the constituent i' comprise(s) at least two organopolysioxanes which differ from each other and which have at least two unsaturated groups in the molecule, where at least one organopolysioxane has a viscosity in the range of from 25 to 500 mPa*s at 25° C., and at least one organopolysiloxane has a viscosity in the range of from 60,000 to 500,000 mPa*s at 25° C.

10. A silicone impression material as claimed in claim 9, wherein constituent (a) contains the at least one organopolysioxane having a viscosity in the range of from 25 to 500 mPa*s at 25° C. in a proportion in the range of from 1 to 5% by weight and the at least one organopolysiloxane, having a viscosity in the range of from 60,000 to 500,000 mPa*s at 25° C. in a proportion in the range of from 10 to 20% by weight.

11. A method for mixing a silicone impression material as claimed in claim 1, wherein the two components are mixed using an automatic motor-driven mixing unit.

12. The method as claimed in claim 11, characterized in that it comprises comprising the following steps:

(A) introducing the components which are contained in primary packs into secondary packs which are compatible with the dimensions of the automatic mixing unit, or introducing the components which are contained in primary packs directly into the automatic mixing unit, or introducing one of the components which is contained in a primary pack into a secondary pack which is compatible with the corresponding dimensions of the automatic mixing unit and directly introducing the component contained in a primary pack into the automatic mixing unit; and (B) discharging the components from the automatic mixing unit by way of a dynamic small mixing tube, while mixing the components, at ejection forces of at most 4000 N.

13. A method of preparing a silicone impression material according to claim 1, the method comprising combining:

(a) from 10 to 25% by weight of at least one organopolysiloxane having at least two unsaturated groups in the molecule and having a viscosity in the range of from 25 to 500 mPa*s at 25° C. and at least one organopolysiloxane having at least two unsaturated groups in the molecule and having a viscosity in the range of from 60,000 to 500,000 mPa*s at 25° C.;

(b) from 1 to 10% by weight of at least one organohydrogenpolysiloxane having at least two SiH groups in the molecule, (c) from 0.00005 to 0.05% by weight of at least one platinum catalyst, calculated as element platinum, (d) from 4 to 10% by weight of at least one liquid paraffin or at least one white mineral oil or of a mixture consisting of at least one liquid paraffin and at least one white mineral oil, and (e) from 50 to 90% by weight of at least one filler having a BET surface area of up to 50 $m^2/g$, in each case based on the total weight of the silicone impression material, characterized in that, in the mixed state, the silicone impression material exhibits a consistency of less than or equal to 35 mm, as determined in accordance with ISO 4823.

14. The method of claim 13, wherein the rheological properties lead to ejection forces of at most 4000 N in an automatic mixing unit which is used for discharging the components and the silicone impression material.

15. A method for adjusting the rheological properties of a silicone impression material, the method comprising combining the first component of claim 1 with the second component of claim 1.

* * * * *

UNITED STATES PATENT AND TRADEMARK OFFICE
CERTIFICATE OF CORRECTION

| | | |
|---|---|---|
| PATENT NO. | : 7,186,758 B2 | Page 1 of 2 |
| APPLICATION NO. | : 10/473282 | |
| DATED | : March 6, 2007 | |
| INVENTOR(S) | : Zech et al. | |

It is certified that error appears in the above-identified patent and that said Letters Patent is hereby corrected as shown below:

Title Page; item (56);

Under Foreign Patent Documents, delete "CA 3406233" and insert --DE 3406233--;

In column 7, line 62, delete "Theological" and insert --rheological--;

In column 8, line 19, delete "Theological" and insert --rheological--;

In column 8, line 22, delete "Theological" and insert --rheological--;

In column 13, line 41 (claim 1), delete "organopolysioxane" and insert --organopolysiloxane--;

In column 14, line 5 (claim 2), delete "organopolysioxane" and insert --organopolysiloxane--;

In column 14, line 8 (claim 2), delete "organohydrogeupolysiloxane" and insert --organohydrogenpolysiloxane--;

In column 14, line 43 (claim 7), delete "(c)" and insert --(e)--;

In column 14, line 64 (claim 9), delete "ease" and insert --case--;

In column 15, line 1 (claim 9), delete "organopolysioxane" and insert --organopolysiloxane--;

In column 15, line 14 (claim 9), delete "organopolysioxanes" and insert --organopolysiloxanes--;

In column 15, line 17 (claim 9), delete "organopolysioxane" and insert --organopolysiloxane--;

In column 15, line 22 (claim 10), delete "organopolysioxane" and insert --organopolysiloxane--;

UNITED STATES PATENT AND TRADEMARK OFFICE
CERTIFICATE OF CORRECTION

PATENT NO. : 7,186,758 B2
APPLICATION NO. : 10/473282
DATED : March 6, 2007
INVENTOR(S) : Zech et al.

It is certified that error appears in the above-identified patent and that said Letters Patent is hereby corrected as shown below:

In column 16, line 21 (claim 13), delete "element" and insert --elemental--.

Signed and Sealed this

Twenty-seventh Day of November, 2007

JON W. DUDAS
*Director of the United States Patent and Trademark Office*